United States Patent
Tropp et al.

(10) Patent No.: US 11,781,986 B2
(45) Date of Patent: Oct. 10, 2023

(54) METHODS FOR DETECTING ANALYTES USING CONJUGATED POLYMERS AND THE INNER FILTER EFFECT

(71) Applicants: Joshua Tropp, Hattiesburg, MS (US); Jason D. Azoulay, Hattiesburg, MS (US)

(72) Inventors: Joshua Tropp, Hattiesburg, MS (US); Jason D. Azoulay, Hattiesburg, MS (US)

(73) Assignee: University of Southern Mississippi, Hattiesburg, MS (US)

( * ) Notice: Subject to any disclaimer, the term of this patent is extended or adjusted under 35 U.S.C. 154(b) by 27 days.

(21) Appl. No.: 17/139,707

(22) Filed: Dec. 31, 2020

(65) Prior Publication Data

US 2021/0293706 A1 Sep. 23, 2021

Related U.S. Application Data

(60) Provisional application No. 62/955,764, filed on Dec. 31, 2019.

(51) Int. Cl.
G01N 21/64 (2006.01)
G16C 20/70 (2019.01)

(52) U.S. Cl.
CPC ........... *G01N 21/645* (2013.01); *G16C 20/70* (2019.02)

(58) Field of Classification Search
CPC .............. G01N 21/645; G01N 21/64; G01N 2021/6432; G01N 2021/6439; G16C 20/70; G16C 20/20; G06N 20/00
See application file for complete search history.

(56) References Cited

U.S. PATENT DOCUMENTS

| 5,510,438 A | 4/1996 | Ferraris et al. |
| 5,552,236 A | 9/1996 | Ohtake et al. |

(Continued)

FOREIGN PATENT DOCUMENTS

| EP | 0223336 A1 | 8/1987 |
| EP | 1756193 B1 | 11/2009 |

(Continued)

OTHER PUBLICATIONS

Tanwar et al. (Receptor free inner filter effect based universal sensors for nitroexplosive picric acid using two polyfluorene derivatives in the solution and solid States, Analyst, 2019, 144, 669).*

(Continued)

*Primary Examiner* — David P Porta
*Assistant Examiner* — Djura Malevic
(74) *Attorney, Agent, or Firm* — Mendelsohn Dunleavy, PC (57) ABSTRACT

The methods disclosed utilize π-conjugated polymers (CPs) as sensors for various analytes through the inner filter effect (IFE). Further, the methods utilize CPs with controlled optical properties for targeting sensing applications and operates through a novel IFE-based method, providing sensitive and selective sensors that operate in complex environments. The methods further provide calibration standards for the identification of similar and structurally distinct target analytes, where the analyte is a small molecule, macromolecule, and/or biological organism of interest.

14 Claims, 9 Drawing Sheets

(56) References Cited

U.S. PATENT DOCUMENTS

| | | | |
|---|---|---|---|
| 5,629,665 A | 5/1997 | Kaumann et al. | |
| 6,083,557 A | 7/2000 | Belcher et al. | |
| 6,262,306 B1 | 7/2001 | Leriche et al. | |
| 6,835,576 B2 | 12/2004 | Matsuzaki et al. | |
| 6,982,514 B1 | 1/2006 | Lu et al. | |
| 8,283,438 B2 | 10/2012 | David et al. | |
| 8,471,204 B2 | 6/2013 | Bornfreund | |
| 8,507,865 B2 | 8/2013 | Boberl et al. | |
| 8,658,751 B2 | 2/2014 | Han et al. | |
| 8,809,487 B2 | 8/2014 | Seferos et al. | |
| 9,035,016 B2* | 5/2015 | Seferos | C08G 61/126 564/426 |
| 9,127,020 B2 | 9/2015 | Hildebrandt et al. | |
| 9,985,211 B2 | 5/2018 | Blouin et al. | |
| 10,426,801 B2* | 10/2019 | Aboody | A61K 47/6923 |
| 10,914,637 B2 | 2/2021 | Lin et al. | |
| 2003/0062480 A1 | 4/2003 | Kanzaki | |
| 2004/0115437 A1 | 6/2004 | Dammann et al. | |
| 2004/0187917 A1 | 9/2004 | Pichler | |
| 2006/0269664 A1 | 11/2006 | Gleason et al. | |
| 2007/0014939 A1 | 1/2007 | Gaudiana et al. | |
| 2007/0111027 A1 | 5/2007 | Chen et al. | |
| 2007/0138945 A1 | 6/2007 | Hoshi et al. | |
| 2007/0181179 A1 | 8/2007 | Brabec et al. | |
| 2010/0181552 A1 | 7/2010 | So | |
| 2010/0221188 A1* | 9/2010 | Clark | G01N 33/66 977/773 |
| 2011/0006287 A1 | 1/2011 | You et al. | |
| 2011/0028656 A1 | 2/2011 | Bazan et al. | |
| 2011/0049367 A1 | 3/2011 | Forrest et al. | |
| 2011/0132460 A1 | 6/2011 | Yang et al. | |
| 2012/0153274 A1 | 6/2012 | Sonar et al. | |
| 2012/0178893 A1 | 7/2012 | Martin et al. | |
| 2013/0032791 A1 | 2/2013 | Bazan et al. | |
| 2013/0092912 A1 | 4/2013 | You | |
| 2013/0225421 A1* | 8/2013 | Li | C12Q 1/686 506/26 |
| 2014/0080717 A1* | 3/2014 | Li | C12Q 1/686 506/26 |
| 2014/0080986 A1 | 3/2014 | Bazan et al. | |
| 2015/0056142 A1 | 2/2015 | Tao et al. | |
| 2016/0118444 A1 | 4/2016 | Liu | |
| 2016/0290998 A1* | 10/2016 | Leif | G01N 33/542 |
| 2017/0069814 A1 | 3/2017 | Bazan et al. | |
| 2017/0324901 A1 | 11/2017 | Mandelli | |
| 2018/0017679 A1 | 1/2018 | Valouch et al. | |
| 2019/0194385 A1 | 6/2019 | Azoulay et al. | |
| 2020/0052216 A1 | 2/2020 | Mitchell et al. | |
| 2020/0095371 A1 | 3/2020 | Tropp et al. | |
| 2020/0362098 A1 | 11/2020 | Azoulay et al. | |
| 2021/0088449 A1* | 3/2021 | Makkad | C08F 112/08 |
| 2021/0293706 A1* | 9/2021 | Tropp | G16C 20/70 |

FOREIGN PATENT DOCUMENTS

| | | |
|---|---|---|
| EP | 1743388 B1 | 3/2012 |
| JP | 2011116961 A | 6/2011 |
| JP | 2013254943 A | 12/2013 |
| JP | 2016065218 A | 4/2016 |
| KR | 10-2015-0113631 A | 10/2015 |
| WO | 99/19883 A1 | 4/1999 |
| WO | 2007016454 A2 | 2/2007 |
| WO | 2011028827 A2 | 3/2011 |
| WO | 2011028827 A3 | 3/2011 |
| WO | 2011052725 A1 | 5/2011 |
| WO | 2011156478 A2 | 12/2011 |
| WO | 2011156478 A3 | 12/2011 |
| WO | 2012136675 A3 | 10/2012 |
| WO | 2012174561 A2 | 12/2012 |
| WO | 2013124688 A3 | 8/2013 |
| WO | 2017125456 A1 | 7/2017 |
| WO | 2017180998 A2 | 10/2017 |
| WO | 2018009924 A1 | 1/2018 |
| WO | 2018039347 A2 | 3/2018 |
| WO | 2018039347 A3 | 3/2018 |
| WO | 2018085055 A1 | 5/2018 |
| WO | 2019012514 A1 | 1/2019 |
| WO | 2022026882 A1 | 2/2022 |

OTHER PUBLICATIONS

Bayreuth et al. (Investigation of the Photophysical Properties of π-Conjugated Polymers A Study by Non-Linear, Time-Resolved, and Single-Molecule Spectroscopy, Tag des Kolloquiums: Apr. 30, 2008).*

Kumar et al. (Challenges and opportunities of polymer design with machine learning and high throughput experimentation, MRS Communications (2019), 9, 537-54, Materials Research Society, 2019).*

International Search Report and Written Opinion for International application No. PCT/US19/30950; dated Mar. 19, 2020 (20 pages).

Guarino, Vincenzo, et al. "Electro-Active Polymers (EAPs): A Promising Route to Design Bio-Organic/Bioinspired Platforms with on Demand Functionalities." Polymers 8.5 Article 185 (2016): 1-26.

Jonas, Friedrich, et al. "Conductive modifications of polymers with polypyrroles and polythiophenes." Synthetic Metals 41.3 (1991): 831-836.

Mirabedini, Azadehsadat, et al. "Developments in conducting polymer fibres: from established spinning methods toward advanced applications." RSC Advances 6.50 (2016): 44687-44716.

Roncali, J. "Molecular Engineering of the Band Gap of π-Conjugated Systems: Facing Technological Applications." Macromolecular Rapid Communications 28.17 (2007): 1761-1775.

Hai, Jiefeng, et al. "Synthesis and photovoltaic performance of novel thiophenyl-methylene-9H-fluorene-based low bandgap polymers" Polymer 54.18 (2013): 4930-4939.

Liu, Jun, et al. "Highly crystalline and low bandgap donor polymers for efficient polymer solar cells." Advanced Materials 24.4 (2012): 538-542.

London, Alexander E., et al. "Donor-acceptor polymers with tunable infrared photoresponse." Polymer Chemistry 8.19 (2017): 2922-2930.

Wu, Zhenghui, et al. "Temperature-Dependent Detectivity of Near-Infrared Organic Bulk Heterojunction Photodiodes." ACS Applied Materials & Interfaces 9.2 (2017): 1654-1660.

Taylor, D. M., et al. "Memory effect in the current-voltage characteristic of alow-band gap conjugated polymer", Journal of Applied Physics, American Institute of Physics, 90.1 (2001): 306-309.

Cheng, Yen-Ju, et al. "Synthesis of conjugated polymers for organic solar cell applications." Chemical Reviews 109.11 (2009): 5868-5923.

Lee, Kwang-hoi, et al. "Synthesis and photovoltaic behaviors of narrow-band-gap π-conjugated polymers composed of dialkoxybenzodithiophene-and thiophene-based fused aromatic rings." Journal of Polymer Science Part A: Polymer Chemistry 49.6 (2011): 1427-1433.

Wu, Zhenghui, et al. "Elucidating the detectivity limits in shortwave infrared organic photodiodes." Advanced Functional Materials 28.18 (2018): 1800391-1800400.

Willot, Pieter, et al. "The Use of Cyclopenta[2,1-b;3,4-b']dithiophene Analogues for the Development of Low-Bandgap Materials." Macromolecular Chemistry and Physics 213.12 (2012): 1216-1224.

Gautier, Christelle, et al. "A poly (cyclopentadithiophene) matrix suitable for electrochemically controlled DNA delivery." Analytical Chemistry 79.20 (2007): 7920-7923.

Kostianovskii, Vladislav A., et al. "Synthesis of novel conjugated polymers comprising modified cyclopentadithiophene units in the main chain." High Performance Polymers 29.6 (2017): 670-676.

Kim, Hyonwoong, et al. "Solution-processed phototransistors combining organic absorber and charge transporting oxide for visible to infrared light detection." ACS Applied Materials & Interfaces 11.40 (2019): 36880-36885.

Benincori, T., et al.: "Steric Control of Conductivity in Highly Conjugated Polythiophenes.." Chemistry of Materials 13.5 (2001): 1665-1673.

(56) References Cited

OTHER PUBLICATIONS

Loganathan, Kavithaa, et al. "Δ4, 4'-Dicyclopenta [2, 1-b: 3,4-b'] dithiophene. A Conjugated Bridging Unit for Low Band Gap Conducting Polymers." Chemistry of Materials 15.9 (2003): 1918-1923.

Berlin, Anna, et al. "New low-gap polymers from 3,4-ethylenedioxythiophene-bis-substituted electron-poor thiophenes. The roles of thiophene, donor-acceptor alternation, and copolymerization in intrinsic conductivity." Chemistry of Materials 16.19 (2004): 3667-3676.

Bünnagel, Torsten W., et al. "A Novel Poly [2, 6-(4-dialkylmethylenecyclopentadithiophene)] with "in-Plane" Alkyl Substituents." Macromolecules 25.39 (2006): 8870-8872.

Pao, Yu-Chieh, et al. "Synthesis and molecular properties of tricyclic biselenophene-based derivatives with nitrogen, silicon, germanium, vinylidene, and ethylene bridges." Organic Letters 16.21 (2014): 5724-5727.

Sabuj, Md. Abdus, et al. "Benzobisthiadiazole-based high-spin donor-acceptor conjugated polymers with localized spin distribution." Materials Advances 2.9 (2021): 2943-2955.

Hou, Jianhui, et al. "Bandgap and molecular energy level control of conjugated polymer photovoltaic materials based on benzo [1, 2-b: 4, 5-b'] dithiophene." Macromolecules 41.16 (2008): 6012-6018.

Extended European Search Report for European application No. 19869325.1; dated Feb. 16, 2022 (21 pages).

Lowe, Andrew B. "Thiol-ene "click" reactions and recent applications in polymer and materials synthesis: a first update." Polymer Chemistry 5.17 (2014): 4820-4870.

Feldman, Kathleen E., et al. "Functional Conducting Polymers via Thiol-ene Chemistry." Biosensors 2.3 (2012): 305-317.

Ibrahimova, Vüsala, et al. "Optical and Electronic Properties of Fluorene-Based Copolymers and Their Sensory Applications." Journal of Polymer Science Part A: Polymer Chemistry 51.4 (2013): 815-823.

Wei, Bin, et al. "Post-polymerization functionalization of poly(3,4-propylenedioxythiophene) (PProDOT) via thiol-ene click' chemistry.", Journal of Materials Chemistry B 3.25 (2015): 5028-5034.

International Search Report and Written Opinion for International application No. PCT/UST2019/052489; dated Jul. 23, 2020 (11 pages).

International Search Report and Written Opinion for International application No. PCT/US21/43986; dated Dec. 27, 2021 (11 pages).

Abdellah, Alaa, et al. "Transfer printed P3HT/PCBM photoactive layers: From material intermixing to device characteristics." ACS Applied Materials & Interfaces 8.4 (2016): 2644-2651.

London, Alex E., et al. "A high-spin ground-state donor-acceptor conjugated polymer." Science Advances 5.5 Article eaav2336 (2019): 1-9.

Vella, Jarrett H., et al. "Broadband infrared photodetection using a narrow bandgap conjugated polymer." Science Advances 7.24 Article eabg2418 (2021): 1-7.

Adams, Daniel, et al., U.S. Appl. No. 63/253,529 filed Oct. 23, 2021. "Molecular and Macromolecular Materials & Compositions Exhibiting Magnetic Anisotropies & Ferromagnetism." (34 pages).

Azoulay, Jasond D., et al. U.S. Appl. No. 63/197,352 filed Jun. 5, 2021. "Infrared Bolometer Based on with Intrinsically Conductive Open-Shell Conjugated Polymers." (23 pages).

Extended European Search Report for corresponding European application No. 19887229.3 dated Jun. 29, 2022 (13 pages).

Davis, Andrew R., et al. "Surface Grafting of Vinyl-Functionalized Poly(fluorene)s via Thiol-Ene Click Chemistry." Langmuir 30.15 (2014): 4427-4433.

Davis, Andrew R., et al. "Controlling Optoelectronic Behavior in Poly(fluorene) Networks using Thiol-Ene Thoto-Click Chemistry." Macromolecules 48.6 (2015): 1711-1722.

Hoyle, Charles E., et al. "Thiol-Ene Click Chemistry." Angewandte Chemie International Edition 49.9 (2010): 1540-1573.

Killops, Kato L., et al. "Robust, Efficient, and Orthogonal Synthesis of Dendrimers via Thiol-Ene "Click" Chemistry." Journal of the American Chemical Society 130.15 (2008): 5062-5064.

Tropp, Joshua, et al. "A sensor array for the discrimination of polycyclic aromatic hydrocarbons using conjugated polymers and the inner filter effect." Chemical Science 10.44 (2019): 10247-10255.

Non-Final Office Action for U.S. Appl. No. 16/404,622; dated Dec. 19, 2022 (13 pages).

\* cited by examiner

METHODS FOR DETECTING ANALYTES USING CONJUGATED POLYMERS AND THE INNER FILTER EFFECT

CROSS-REFERENCE TO RELATED APPLICATION

This application claims priority from U.S. Provisional Patent Application Ser. No. 62/955,764 filed Dec. 31, 2019. The entirety of the provisional application is incorporated herein by reference.

STATEMENT OF GOVERNMENT SUPPORT

This invention was made with government support under grant/contract number OIA-1632825 awarded by the National Science Foundation. The government has certain rights in the invention.

FIELD OF THE INVENTION

The methodology disclosed relates to chemical sensing and novel methods and processes for detecting diverse analytes and mixtures of analytes. The methods utilize π-conjugated polymers with controlled optical properties to detect and discriminate analytes through the inner filter effect and data processing techniques.

SUMMARY OF THE INVENTION

The methods and processes provide for utilizing π-conjugated polymers with controlled optical properties for the detection of small molecule, macromolecular, and biological analytes. The chemical sensors operate through an inner filter effect due to the similar optical properties of the π-conjugated polymers and analytes. Data analysis may proceed via multivariate techniques, allowing for the discrimination of similar and different analytes. The novel methodologies provide approaches for the detection, discrimination, and quantification of both individual and mixtures of optically active analytes in various chemical environments.

BACKGROUND OF THE INVENTION

Solution-processable organic semiconductors based on small molecules and polymers have provided a new generation of optoelectronic technologies owing to their modularity, distinct manufacturing paradigms, diverse optical and transport properties, and opportunities for innovation not possible using inorganic materials. Significant technological milestones have been achieved such as commercially available organic light emitting diodes, infrared photodetectors that do not require cryogenic cooling, printed electronic devices, biocompatible medical materials, and sensing technologies that were previously unimaginable. Organic semiconductor-based sensors utilize fluorescent conjugated polymers (CPs) and conjugated polyelectrolytes (CPEs) which can simultaneously function as molecular recognition and signal transduction elements for analyte detection, which display unique signal amplification characteristics when compared to small molecule sensors, leading to orders of magnitude improvements in sensitivity. For example, the modularity, stability, and low detection limits of these systems are ideal for applications in food and water quality monitoring, medical analysis, environmental monitoring, precision agriculture, etc. Widespread interest in CP sensing technologies has further motivated research efforts aimed at expanding the scope and sensitivity of these materials and technologies. CPs transduce signals through the migration of excitons which are relatively immune to electrostatic and dielectric variations, allowing their successful implementation for sensing applications within complex environments. The diffusing exciton is captured through binding events along the polymer, resulting in the collective response of each repeat unit within the exciton diffusion length. The exciton diffusion process and correlated optical response are closely related to the electronic and structural conformation of the polymer backbone, which can be synthetically tuned to incorporate molecular design features that enhance exciton delocalization, leading to stronger amplified signals and low limits of detection. These mechanisms are distance dependent and require CP-analyte interactions that are facilitated through the incorporation of receptors within, or extended from, the CP backbone. The lack of specific recognition elements for challenging analytes, and of electronically coupling analyte-receptor interactions into transducible optical responses, complicates the development of optical sensing platforms capable of profiling many analytes in complex mixtures. These downfalls are fundamentally associated with the nature of signal transduction typically employed within CP-based sensing platforms.

More recently, array-based sensing has been used to profile combinations of structurally and chemically similar analytes through multivariate pattern recognition. Subtle structural differences between nonspecific CP-based sensors allow for differential interactions with analytes that establish identifying optical responses, which creates a "chemical fingerprint" used to discriminate similar compounds using pattern recognition algorithms to highlight and summarize distinguishing features in large data sets leading to chemical differentiation. Current array-based CP sensors utilize traditional analyte-driven responses requiring complex recognition elements, thereby limiting their scope.

The inner filter effect (IFE) results from the absorption of light by a chromophore in solution, preventing photons from reaching a fluorophore, creating an observed decrease in fluorescence emission. Sensing platforms operating through the IFE rely on the spectral overlap between the sensor and the analyte rather than traditional host-guest chemistries, circumventing the need for tailored receptors. CP-based sensors have been recently reported utilizing the IFE for the detection of contaminants, however the use of the IFE alone is nonspecific and does not allow for the differentiation of similar analytes.

Despite the advantages and vast number of reports in the sensing literature using CPs, the advantages of both array-based sensing and the IFE have not been leveraged in CP-based sensors. Sensors and a system that utilize the unique signal transduction of the IFE, coupled with machine-learning data processing, would address the problems associated with CP-based sensors. The methodology described herein provides such solutions.

DESCRIPTION OF EMBODIMENT(S)

The present invention provides new methods and processes for the preparation and utilization of conjugated polymer (CP) based sensors which operate via the inner filter effect (IFE) and multivariate pattern recognition. Further, the invention provides methods of utilizing CPs with controlled optical properties for targeted sensing applications. The invention proceeds through a novel IFE array-sensing method, providing sensitive and selective sensors that can be used in various environments. The invention further provides calibration standards for the identification of similar and structurally distinct target analytes, where an analyte is a small molecule, macromolecule, or biological organism of interest.

Specifically, the invention provides methods of detecting one or more analyte(s) using at least one π-conjugated polymer (CP) as a sensor, whereby and wherein the fluorescence of the at least one π-conjugated polymer (CP) is altered by the analyte(s). Fluorescence is the emission of electromagnetic radiation; here, the polymer emits electromagnetic radiation which can be monitored as the signal for detection. Detection is defined as identifying the presence of a substance or sample, also known as an analyte, as well as identifying what specific analyte the substance is, i.e., the presence and the identification of the analyte. The detection of the analyte(s), or the discrimination of different analytes, is defined as the data or knowledge that analyte(s) exists or is present and the data, knowledge, or identification of what type of analyte(s) are present.

In one embodiment, a conjugated polymer and an analyte are mixed in a liquid solution, i.e., the same solution. Electromagnetic radiation, i.e., energy, is applied to the solution and therefore also to the polymer. The liquid solution can be static (not moving or flowing) or dynamic (moving or flowing). Light is shined through the solution and radiation is detected. The analyte(s) change or attenuate the radiation or fluorescence of the polymer (quenching) by absorbing the electromagnetic radiation used to excite the polymer, or by absorbing the emitted electromagnetic radiation from the polymer, which is known as the Inner Filter Effect (IFE). As the IFE operates through space and does not require a physical interaction, the polymer and the analyte(s) can be mixed together in a solution or separated in this method. Depending on the structure and optical properties of the polymer and the analyte, there are differences in fluorescence quenching. One or more analytes can be detected by using multiple polymers that are quenched differently by each analyte. The method enables the measurement of the attenuated fluorescence from the polymer, followed by processing and/or analysis, by at least one algorithm or means of processing, from a plurality of algorithms or means of processing, via a computer-based or micro-processor-based device and/or a non-transitory computer-readable medium, the attenuated fluorescence data to detect the presence and/or the type of the analyte. The algorithm or means of processing may comprise at least one machine learning algorithm.

In other embodiments, the polymer and the analyte may be placed in different solutions such that the polymer is not mixed with the analyte in the same solution and the polymer and analyte do not touch each other. The polymer is or can be placed in a first solution and the analyte placed in a separate, second solution, wherein the first solution consists of or is made of a different solvent than the second solution, such that the polymer and the analyte are in their own respective, individual solutions. Alternatively, the two individual first and second solutions may consist of or are made of the same solvent. Further, the first solution may be static and the second solution may be dynamic, or vice versa, or, alternatively, both solutions may be static or both solutions may be dynamic. Light can be passed through both solutions to provide fluorescence quenching for detecting and/or the discrimination of analyte(s).

The concentration of the analyte that can be detected from this method is referred to as the sensitivity. The lower the concentration of an analyte that can be detected, the greater the sensitivity of the sensor provided by the method. The concentration of the analyte that may be detected using this method ranges from femtomolar concentrations, to nanomolar, micromolar, millimolar, and to molar concentrations and above.

The collected fluorescence data is or can be processed through common and widely accessible multivariate pattern recognition algorithms, such as Linear Discriminant Analysis (LDA) and Principal Component Analysis (PCA), for example. These algorithms process the collected data and reduce the size and complexity, allowing for the discrimination of multiple analytes. The output of the algorithm is or can be a two-dimensional scores plot, which visualizes the discrimination of each analyte and acts as a calibration plot of the sensor, and a two-dimensional loadings plot, which describes how the algorithm generated the scores plot. Visualization is and provides a generated graphical plot for viewing or visualizing the analyte data and the discrimination or detection of each analyte. The discrimination of multiple analytes is or can be visualized by an algorithm, from a plurality of algorithms, that comprises at least one machine learning algorithm. An algorithm is not necessary in the case wherein only one analyte is to be detected.

The methods provide several advantages compared to traditional CP-based sensing approaches: 1) the new methodology overcomes the use of receptor chemistries and host-guest interactions typically utilized in CP-based sensors; 2) the use of the IFE avoids solvent dependent behavior typically associated with CP-based sensors; 3) the methods provide sensors which can be used in both the solution state and the solid state; 4) unique sensitivities of multivariate pattern recognition algorithms can be employed to circumvent the lack of selectivity in systems utilizing the IFE; and 5) the methodology allows for the discrimination of structurally similar analytes without the need of spatially distinct, parallel sensor elements. These advantages, coupled with the highly tunable nature of CPs, permit access to sensors with a diverse scope previously unattainable using CP-based sensing platforms. The methods have high potential for utilization in sensing technologies including, but not limited to, food and water quality monitoring, medical analysis, environmental monitoring, precision agriculture, and other sensing applications.

1. In one embodiment, a method for utilizing π-conjugated polymers (CPs) with controlled optical properties for the detection of one or multiple analytes is provided comprising mixing at least one CP with one or more than one type of analyte. In some embodiments, the CP is a homopolymer, which is a polymer that has the same monomer unit throughout the chain or is composed of monomers all of the same type. In other embodiments, the repeat unit of the CP contains two or more different monomers and is therefore defined as a copolymer. The monomers that make up such CPs comprise or consist of a single type or multiple types of arenes, heteroarenes, unsaturated linkers, or a combination thereof.

"Arene" (Ar) is defined as an optionally substituted aromatic ring system, such as phenyl or naphthyl. Arene groups include monocyclic aromatic rings and polycyclic aromatic ring systems. In other embodiments, arene groups can be unsubstituted. In yet other embodiments, arene groups can be substituted.

"Heteroarene" is defined as an optionally substituted aromatic ring system where heteroatoms include, but are not limited to, oxygen, nitrogen, sulfur, selenium, tellurium, phosphorus, etc. In other embodiments, heteroaryl groups can be unsubstituted. In other embodiments, heteroarene groups can be substituted.

"Unsaturated linker" is defined as an alkyne or optionally substituted alkene unit that connects substituted arenes, substituted heteroarenes, unsubstituted arenes, unsubstituted heteroarenes, or a combination thereof.

"Analyte" is defined as a component, chemical species, or chemical constituent that is of interest and includes, but is not limited to, small molecules, oligomers, macromolecules, biomacromolecules, biological organisms, nutrients, anions, cations, toxicants, nanomaterials, or a combination thereof.

2. In one embodiment, the method utilizes polymers of the formula (I):

where Ar is an arene or (hetero)arene as defined above; R is selected from the group consisting of: variable length, linear or branched, aliphatic ethylene glycol chains or halogen-containing or heteroatom-containing chains of length n, where n is an integer value, unsubstituted hydrocarbyl, substituted hydrocarbyl, unsubstituted aryl, substituted aryl, unsubstituted heteroaryl, substituted heteroaryl, unsubstituted hydrocarbylene, hydrocarbyl, and substituted hydrocarbylene, hydrocarbyl, $R^2F$, $R^2Cl$, $R^2Br$, $R^2I$, $R^2CN$, $—R^2$, $—R^2OH$, $—R^2OR^3$, $—R^2COOH$, $—R^2COOR^3$, $—R^2NH_2$, $—R^2NHR^3$, $R^2NR^3R^4$, $—R^2SO_3^-$, $—R^2NH_3^+$, or $—R^2COO^-$, and other charged functionalities, where $R^2$, $R^3$, and $R^4$ are independently selected from a hydrocarbyl group or an ethylene glycol-based group; R can be any functional group; and n is an integer between about 10 and about 1000.

Functionalization thereof can occur at one or more than one location on the arene or heteroarene repeat unit.

3. In another embodiment, the method utilizes copolymers of the formula (II):

where Ar and $Ar_2$ are arenes or (hetero)arenes as defined above, where Ar and $Ar_2$ are different in identity; R is selected from the group consisting of: variable length, linear or branched, aliphatic ethylene glycol chains or halogen-containing or heteroatom-containing chains of length n, where n is an integer value, unsubstituted hydrocarbyl, substituted hydrocarbyl, unsubstituted aryl, substituted aryl, unsubstituted heteroaryl, substituted heteroaryl, unsubstituted hydrocarbylene, hydrocarbyl, and substituted hydrocarbylene, hydrocarbyl, $R^2F$, $R^2Cl$, $R^2Br$, $R^2I$, $R^2CN$, $—R^2$, $—R^2OH$, $—R^2OR^3$, $—R^2COOH$, $—R^2COOR^3$, $—R^2NH_2$, $—R^2NHR^3$, $R^2NR^3R^4$, $—R^2SO_3^-$, $—R^2NH_3^+$, or $—R^2COO^-$, and other charged functionalities, where $R^2$, $R^3$, and $R^4$ are independently selected from a hydrocarbyl group or an ethylene glycol-based group; R can be any functional group; and n is an integer between about 10 and about 1000.

4. In another embodiment, the method utilizes conjugated polymers of the formula (III):

where UL is an unsaturated linker such as an alkyne or optionally substituted alkene unit that connects substituted arenes, substituted heteroarenes, unsubstituted arenes, unsubstituted heteroarenes, or a combination thereof; R is selected from the group consisting of: variable length, linear or branched, aliphatic ethylene glycol chains or halogen-containing or heteroatom-containing chains of length n, where n is an integer value, unsubstituted hydrocarbyl, substituted hydrocarbyl, unsubstituted aryl, substituted aryl, unsubstituted heteroaryl, substituted heteroaryl, unsubstituted hydrocarbylene, hydrocarbyl, and substituted hydrocarbylene, hydrocarbyl, $R^2F$, $R^2Cl$, $R^2Br$, $R^2I$, $R^2CN$, $—R^2$, $—R^2OH$, $—R^2OR^3$, $—R^2COOH$, $—R^2COOR^3$, $—R^2NH_2$, $—R^2NHR^3$, $R^2NR^3R^4$, $—R^2SO_3^-$, $—R^2NH_3^+$, or $—R^2COO^-$, and other charged functionalities, where $R^2$, $R^3$, and $R^4$ are independently selected from a hydrocarbyl group or an ethylene glycol-based group; R can be any functional group; and n is an integer between about 10 and about 1000.

Functionalization thereof can occur at one or more than one location on the arene or heteroarene monomer of the repeat unit.

For formulas I through III above, the size of the utilized polymers, including their molecular weight, may or may not vary widely from each other, depending on the properties desired. In some embodiments, n is an integer of at least about 10, at least about 20, at least about 50, or at least about 100. In some embodiments, n is an integer between about 5 and about 10,000, between about 10 and about 10,000, between about 10 and about 5,000, between about 10 and about 2,500, between about 10 and about 1,000, between about 10 and about 500, between about 50 and about 10,000, between about 50 and about 5,000, between about 50 and about 2,500, between about 50 and about 1,000, between about 50 and about 500, between about 100 and about 10,000, between about 100 and about 5,000, between about 100 and about 2,500, between about 100 and about 1,000, or between about 100 and about 500. Other intervals, combining any of the above numerical parameters to form a new interval, can also be used (e.g., n between about 500 and 2,500).

5. In additional embodiments, the method utilizes conjugated oligomers which are polymer compound(s) ten (10) units long and below, wherein oligomer(s) of size n are formed and wherein n is an integer between 1 and 10 and n is not 1.

Some embodiments described herein are recited as "comprising" or "comprises" with respect to their various elements. In alternative embodiments, those elements can be recited with the transitional phrase "consisting essentially of" or "consists essentially of" as applied to those elements. In further alternative embodiments, those elements can be recited with the transitional phrase "consisting of" or "consists of" as applied to those elements. Thus, for example, if a composition or method is disclosed herein as comprising A and B, the alternative embodiment for that composition or method of "consisting essentially of A and B" and the alternative embodiment for that composition or method of "consisting of A and B" are also considered to have been disclosed herein. Likewise, embodiments recited as "consisting essentially of" or "consisting of" with respect to their various elements can also be recited as "comprising" as applied to those elements.

6. In additional embodiments, the method utilizes conjugated polymers as described in embodiments 1-5 above, but which are utilized in a solid state material for detection and/or discrimination of an analyte(s). The analyte is or can be immobilized with the conjugated polymer wherein the polymer is or can be incorporated within a solid state material, wherein the solid state is defined as being incorporated in a solid state material that includes, but is not limited to, a membrane, film, polymer resin, filter, paper, coating, or inorganic or organic mixture. In each of these solid states, the conjugated polymer is or can be mixed with or immobilized in a matrix or any class of organic polymer or inorganic compound or material. Thus the polymer, rather than the analyte, can be immobilized or stationary. The analyte is or can be spatially separated from and layered or located above, below, or on any side of the polymer in the solid state material or the solid state conjugated polymer structure, where electromagnetic radiation is passed through or passes through both the analyte and the polymer in the solid state material.

Additionally, for detection and/or discrimination of an analyte(s), the analyte is or can be incorporated within a solid state material, rather than the polymer as described above, wherein the solid state material is comprised of or includes, but is not limited to, a membrane, film, polymer resin, filter, paper, coating, or inorganic or organic mixture. Likewise, in each of these solid states, the analyte is or can be mixed with or immobilized in a matrix or any class of organic polymer or inorganic compound or material. Electromagnetic radiation is likewise passed through or passes through both the polymer and analyte in the solid state material.

7. In additional embodiments, the method can discriminate between multiple or single analytes using conjugated polymers as described in embodiments 1-6, and can utilize at least one commercial or modified algorithm, including machine learning algorithm(s), through the input of the collected optical data. Such machine learning algorithms include, but are not limited to, hierarchical cluster analysis, principal component analysis, linear discriminant analysis, support vector machines, artificial neural networks, and other statistical descriptive and classification methods.

Certain differences between solution and solid state detection, corresponding to Examples 1 through 3 below, respectively, are as follows:

(1) One embodiment is the method of detection wherein both the analyte and the polymer are in the same solution. A solution is a liquid mixture in which one or more compound (s) (minor component, solute) is/are dissolved in a solvent. The polymer and the analyte sample are mixed in a solvent to form a solution. Light (radiation) is shined into the sample/solution, and emitted radiation (fluorescence) is collected. The collected light is used to identify the analyte.

(2) Another embodiment is the method of detection wherein light is shined into or through both the analyte and polymer, where the analyte and the polymer do not need to be touching (mixed in the same solution). This allows the mixing of the polymer into separate phases. Here, the polymer is mixed with a solid-state substance (polymer, paper, membrane, etc.). The polymer is not a solid-state, but is in a solid-state substance (polymer, paper, membrane, etc.). This is what is defined by the description of the conjugated polymer being in the solid state for the detection of analyte(s). Light is shined through the polymer that is in the solid state substance and is also shined through the sample (analyte), which is not mixed with the polymer in the solid state substance. As in (1) above, emitted radiation is collected from the sample (fluorescence). The collected radiation is used to identify the analyte.

(3) Another embodiment is similar to (2) above, but with the analyte in the solid-state substance rather than the polymer.

In the examples above (2 and 3), the polymer and the analyte are not mixed. One, either the polymer or the analyte, is immobilized (trapped) in a solid-state substance, while the other is in solution, and vice-versa for the other case. Light travels through both and therefore the polymer sensor can operate as designed.

EXAMPLES

Three examples are as follows: All spectra were recorded at ambient temperature, unless otherwise stated. UV-vis absorbance measurements were performed on a Hewlett-Packard 8452a diode array UV-vis spectrophotometer. Benchtop steady-state fluorescence measurements were carried out with an ISS PCI spectrofluorimeter. Excitation was carried out using a broad-spectrum high-pressure xenon lamp (CERMAX, 300 W). Excitation correction was performed through a rhodamine B quantum counter with a dedicated detector. Detection was through a Hamamatsu red-sensitive PMT. High-aperture Glan-Thompson calcite polarizers were used in the excitation and emission channels to measure steady-state fluorescence anisotropy. Experimental temperature (25° C.) was controlled by an external circulating water bath. Multivariate data was acquired on a BioTek Synergy II multimode microwell plate reader, capable of measuring absorption spectra through a monochromator and steady-state fluorescence intensity measurements through a set of bandpass filters. The sample compartment in this instrument was electrically thermostatted to 25° C.

Example 1

Figure 1:
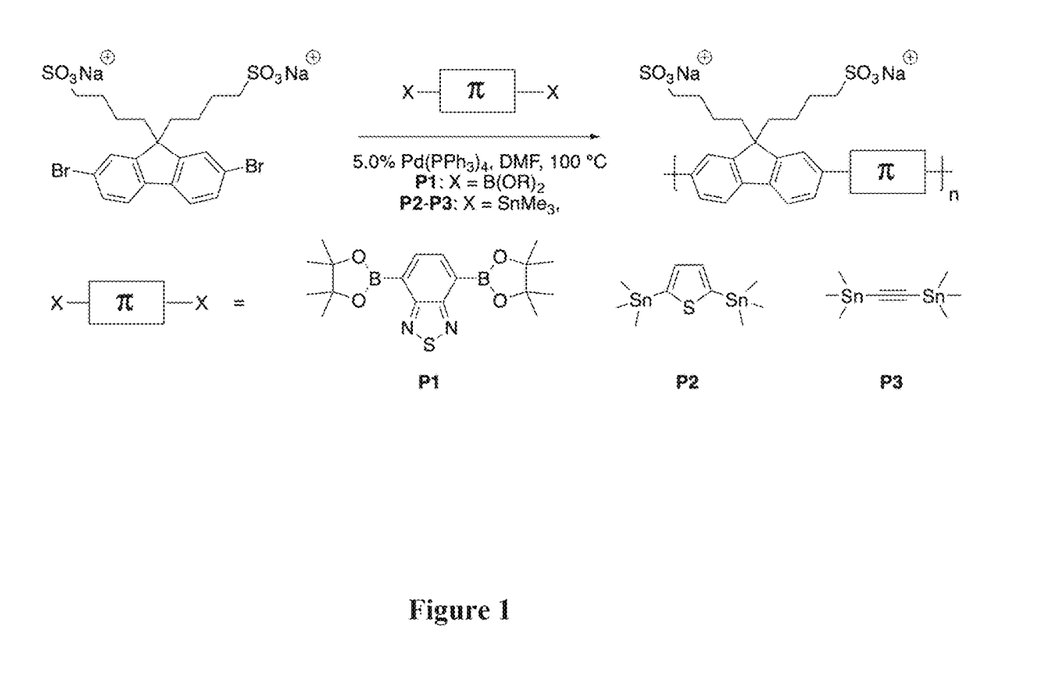
FIG. 1 shows the synthesis and chemical structures of the conjugated polymers P1-P3.
Figure 2:
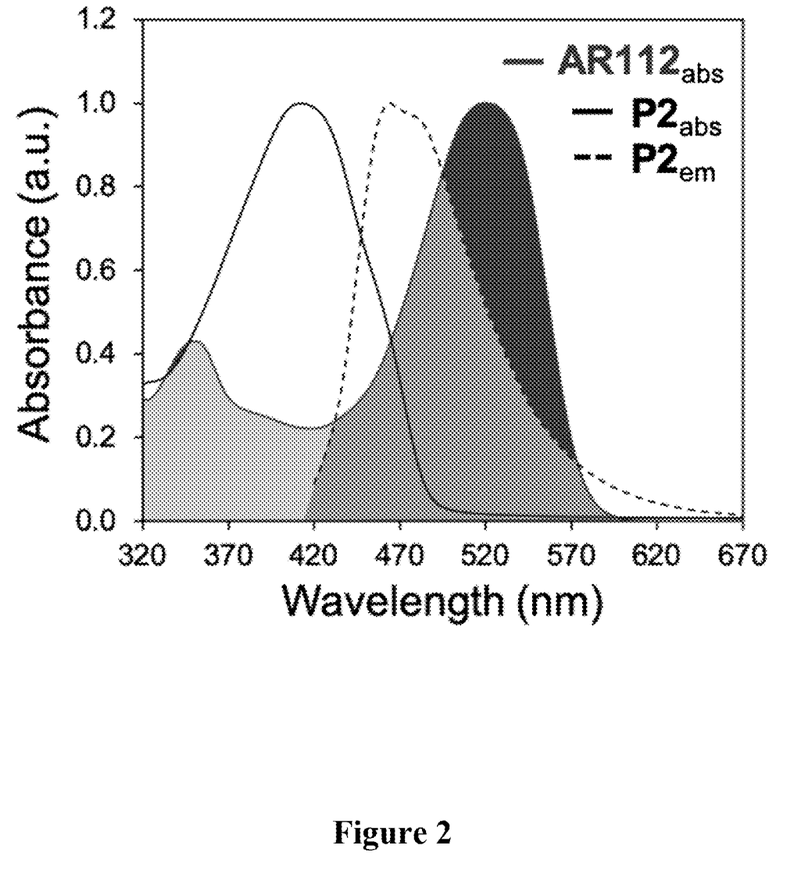
FIG. 2 shows a graphical representation of the UV-Vis absorption spectrum of polymer P2 and Acid Red (AR) 112.
Figure 3:
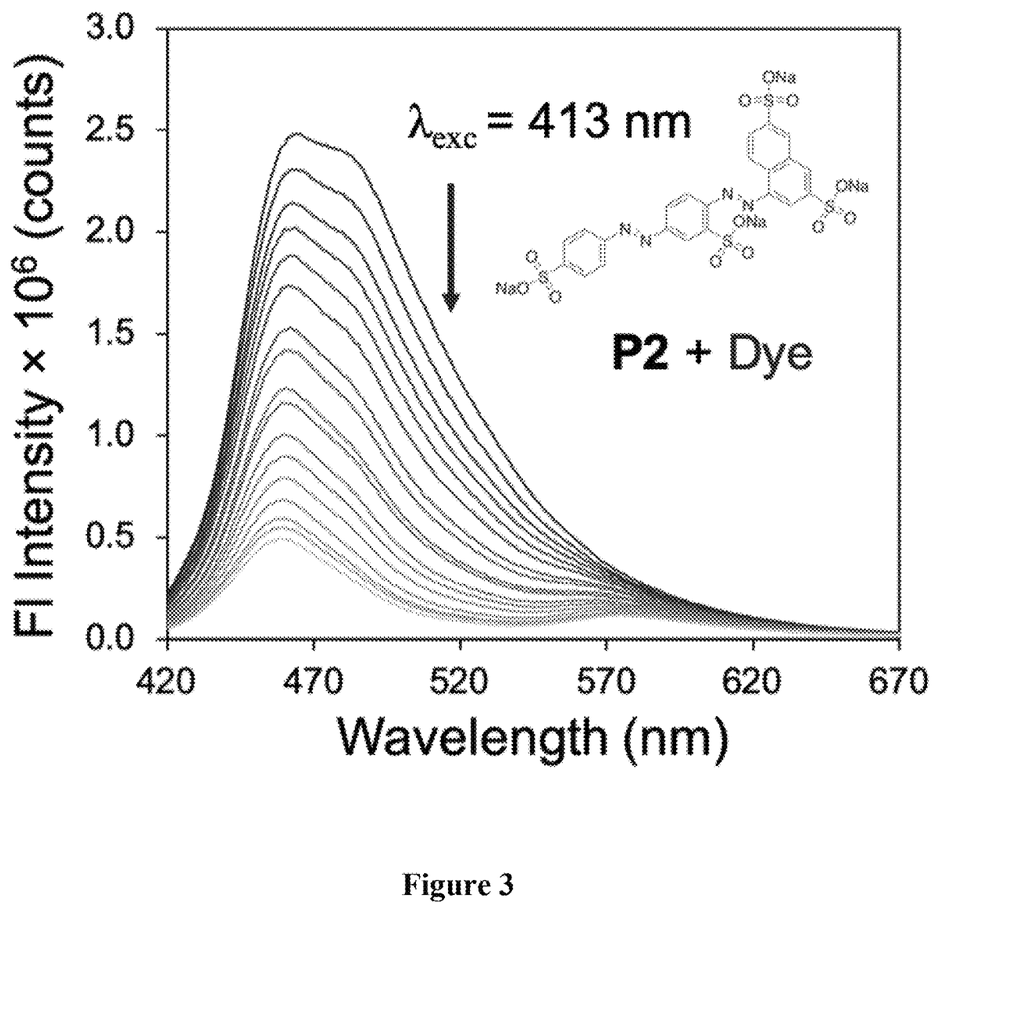
FIG. 3 shows a graphical representation of the fluorescence spectrum of polymer P2 upon titration with Acid Red (AR) 112.
Figure 4:
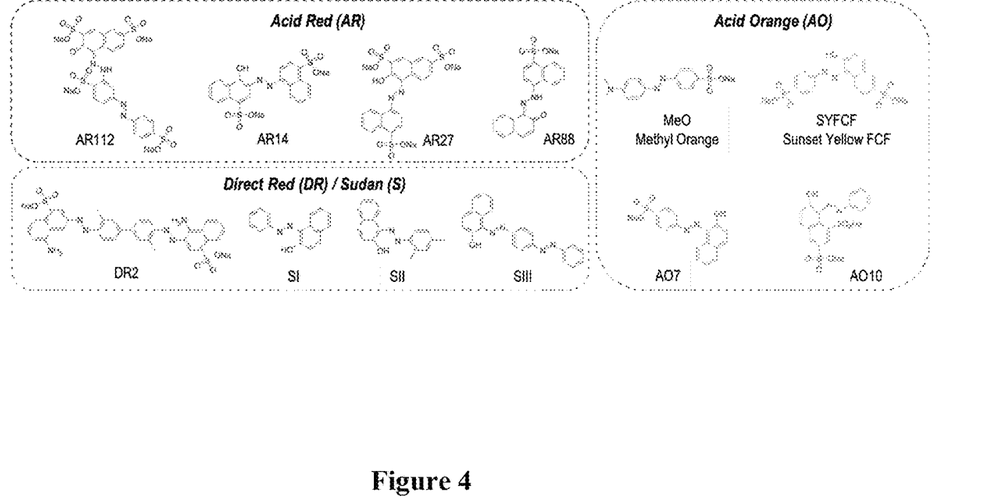
FIG. 4 shows a structural representation of the 12 target dye analytes detected using polymers P1-P3 using the inner filter effect, linear discriminant analysis, and principal component analysis.

Example 1 involved the detection of Acid Red 112 using polymer P2 and the inner filter effect. Polymer P2 and Acid Red 112 stock solutions were prepared separately, then 3 mL of the polymer solutions in $H_2O$ was inserted into a quartz cuvette, and absorption and fluorescence spectra were collected for P2. Fluorescence emission spectra were collected by exciting the polymer at 413 nm. Binding titrations were performed by adding aliquots (10 μL per addition) of dye solution in $H_2O$ to the polymer. Apparent quenching of fluorescence demonstrated detection of the dye through the inner filter effect. FIG. 1 shows the identity and structures of conjugated polymers P1-P3. FIG. 2 shows the normalized excitation and emission spectra of P2 overlaid with normalized Acid Red 112 absorption ([Acid Red 112]=10 μM; [P2]=10 μM), providing the basis for an IFE as there is spectral overlap between optical properties of the conjugated polymer, and the analyte Acid Red 112. FIG. 3 shows the fluorescence spectra of P2 (10 μM) upon titration with Acid Red 112 (0-62.8 μM) in deionized (DI) water ($\lambda_{exc}$=413 nm). The decrease in fluorescence of P2 upon titration of Acid Red 112 is due to the Inner Filter Effect and is the collected signal of the sensor. FIG. 4 shows the structures of 12 target dye analytes detected using polymers P1-P3. In FIGS. 1-9, "AR" represents Acid Red, "DR" represents Direct Red, and "AO" represents Acid Orange.

Example 2

Figure 5:
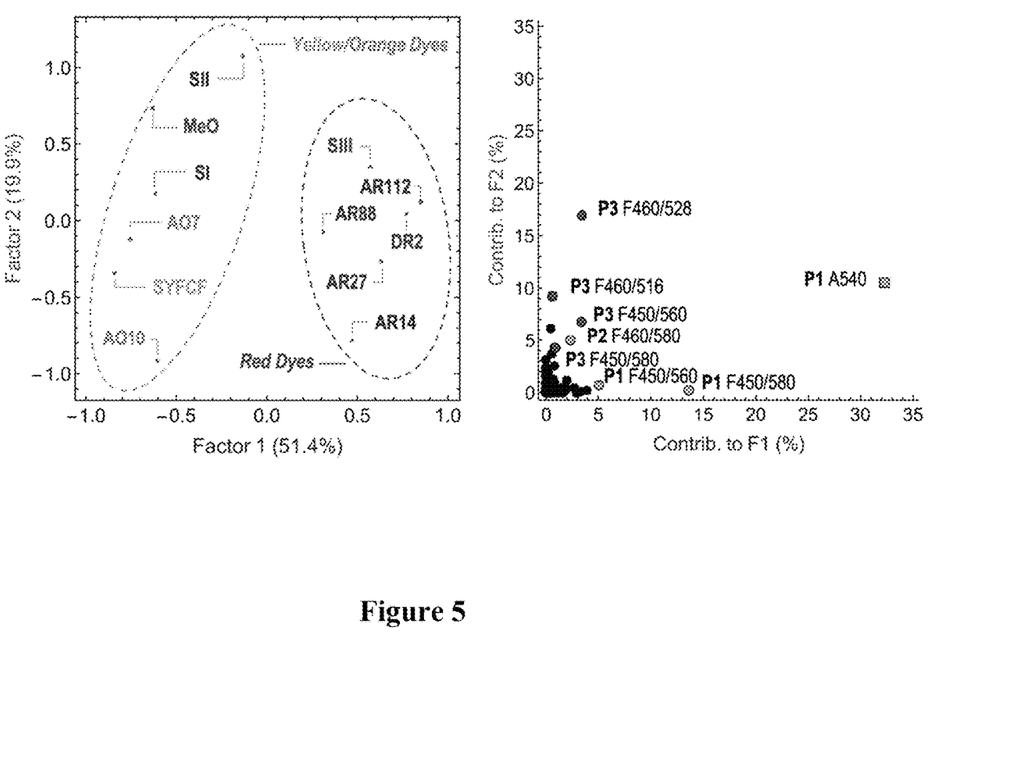
FIG. 5 shows the two-dimensional scores and loadings plots from linear discriminant analysis which graphically represents the data processing for the detection of the 12 target dye analytes with polymers P1-P3.
Figure 6:
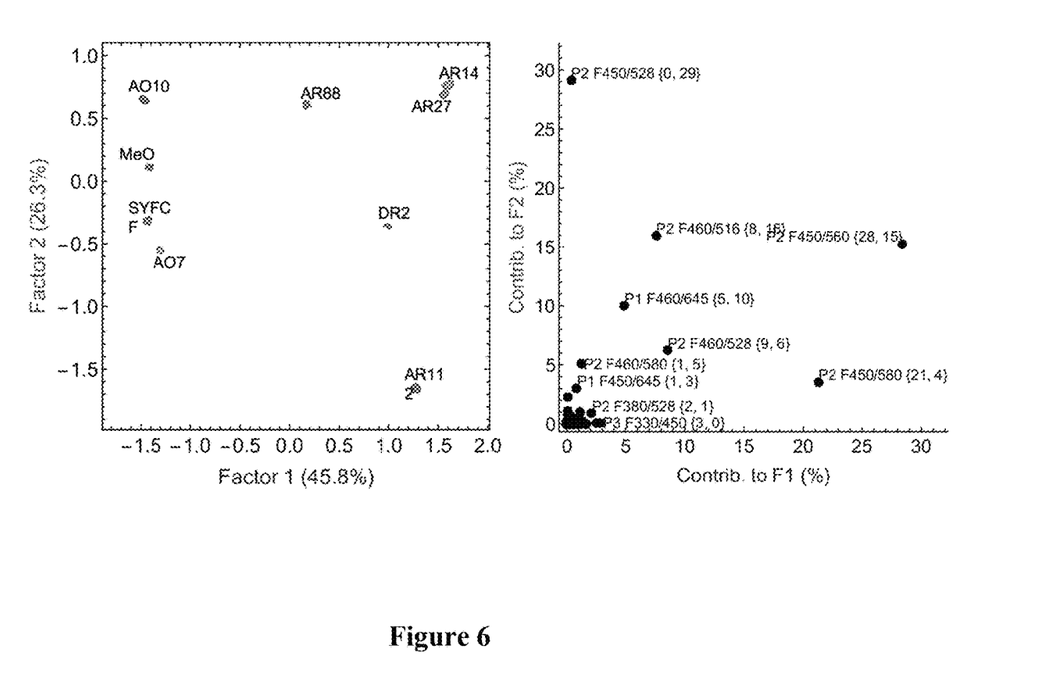
FIG. 6 shows the two-dimensional scores and loadings plots from principal component analysis which graphically represents the data processing for the detection of the 12 target dye analytes with polymers P1-P3.

Example 2 involved the detection of 12 dye analytes using polymers P1-P3, the inner filter effect, linear discriminant analysis, and principal component analysis. Solutions of P1-P3 in $H_2O$ (15 μM) were arranged on a 384-well plate and exposed to 20 μM solutions of each dye (see FIG. 4) in $H_2O$. Experiments were laid out by hand using Eppendorf Research multichannel pipettors and disposable plastic tips into Aurora microwell plates with clear bottoms for UV absorption and fluorescence spectroscopy in a 384-well configuration. The plates were made of non-treated cyclo-olefin polymer (COP) with clear flat bottoms. Each well was filled with (100 μL) of the sample solution. Plates were read on a multimode plate reader immediately after preparation. Absorbance (A) and fluorescence (F) data were processed through linear discriminant analysis and principal component analysis to create calibration plots for the detection and discrimination of 12 dye analytes. FIG. 5 shows a representation of the graphical outputs from linear discriminant analysis to process the detection of the 12 target dye analytes with P1-P3. The plot on the left is a two-dimensional scores plot, which visualizes the discrimination of each analyte and acts as a calibration plot of the sensor, and the plot on the right is a two-dimensional loadings plot, which describes how the algorithm generated the scores plot. FIG. 6 shows a representation of the graphical output from principal component analysis to process the detection of the 12 target dye analytes with P1-P3. The plot on the left is a two-dimensional scores plot, which visualizes the discrimination of each analyte and acts as a calibration plot of the sensor, and the plot on the right is a two-dimensional loadings plot, which describes how the algorithm generated the scores plot.

Example 3

Figure 7:
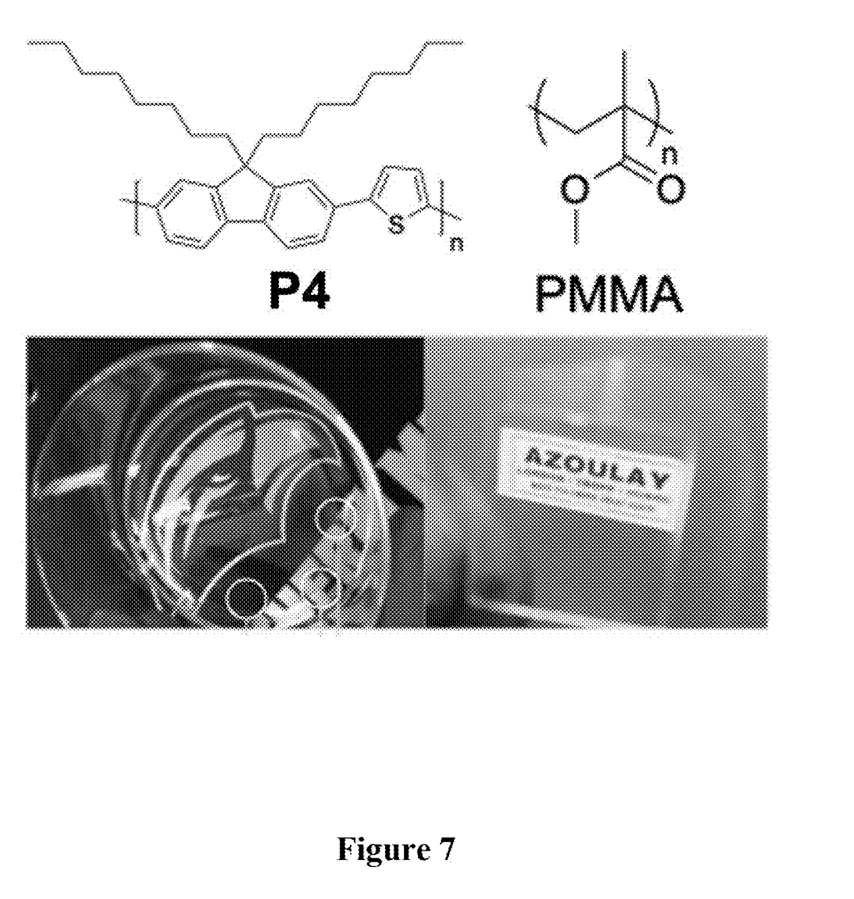
FIG. 7 shows the identity and structure of conjugated polymer P4 and a representative example of a solid-state polymer sensor.
Figure 8:
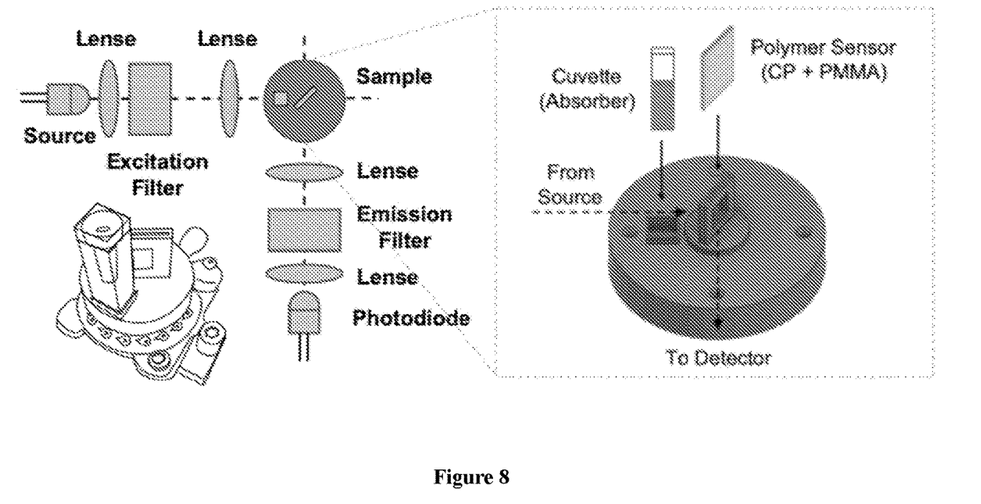
FIG. 8 shows a pictorial representation demonstrating the operation of a solid-state sensor using the inner filter effect to detect a spatially separated analyte.
Figure 9:
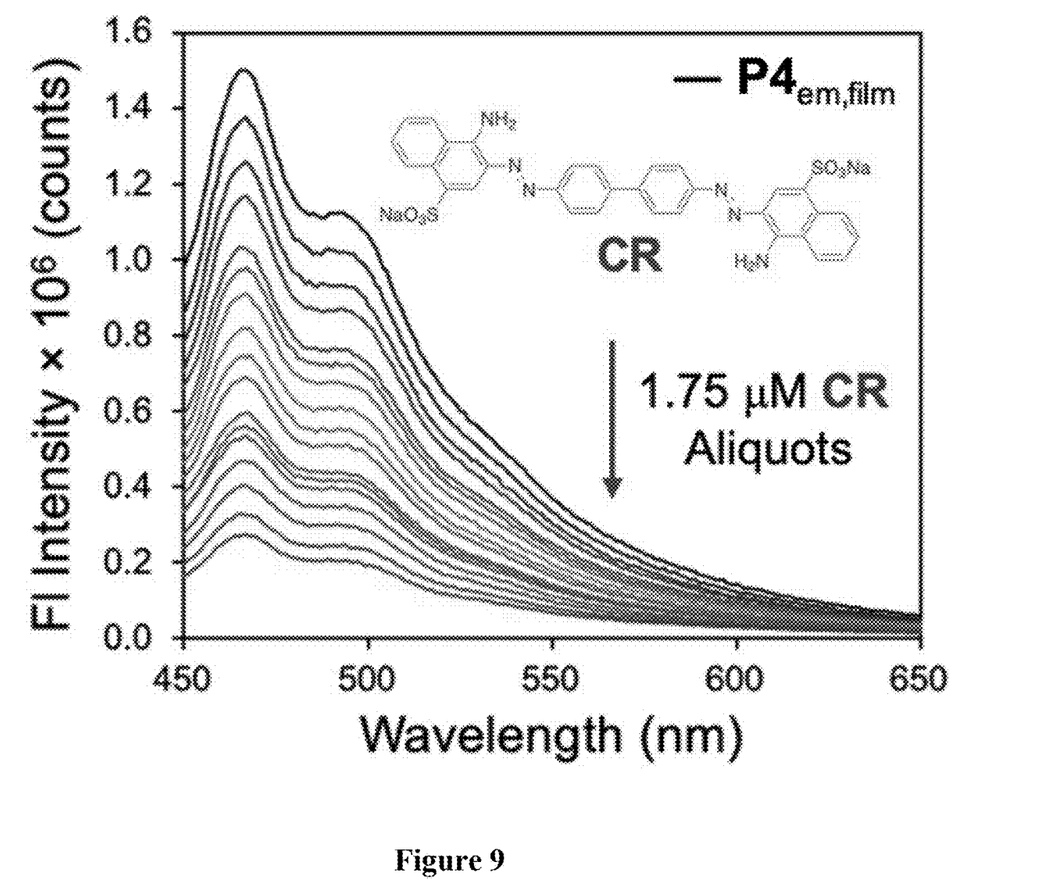
FIG. 9 shows a graphical representation of the fluorescence spectrum of polymer P4 in the solid-state upon titration with Congo Red (CR).

Example 3 involved the detection of an azo dye using polymer P4 and the inner filter effect wherein the polymer is in the solid state and spatially separated from the analyte. Solid state sensors were developed by embedding poly[2,5-(thienylene)-2,7-(9,9-dioctylfluorene)] (P4) into poly (methyl methacrylate) (PMMA). P4 and PMMA were dissolved and stirred together in methylene chloride, mixed for 1 h, and the solvent was evaporated overnight affording a transparent film (FIG. 7). The resulting mixture was ground into pellets and heated in an oven to remove residual solvent, and processed using a Carver benchtop hydraulic press (4386 Carver Inc., Wabash, Ind., U.S.A.) to afford smooth, optically transparent solid-state polymer films (FIG. 7) which were then used as the solid-state sensor. FIG. 8 outlines a general diagram of the incident beam path to operate the solid-state sensor when spatially separated from the analyte. A sample holder was printed via additive manufacturing to allow for the incident light to travel first through the analyte in a cuvette, and then through the solid-state sensor (see FIG. 8). Congo Red dye stock solutions were prepared separately and titrated into a cuvette spatially separated from the solid-state polymer sensor (0-26.3 μM) in deionized (DI) water. FIGS. 7 and 8 show the polymer sensor operating in the solid-state. This is not a separate potential detection pathway, but is one detection pathway and a separate application of the same detection pathway. FIG. 9 shows the fluorescence emission spectra collected by exciting the polymer sensor at 435 nm using 1.75 μM aliquots of Congo Red solution. Apparent quenching of fluorescence demonstrates detection of the dye through the inner filter effect when the analyte is spatially separated from the polymer sensor.

All parameters presented herein including, but not limited to, temperatures, pressures, volumes, dimensions, times, sizes, amounts, distances, quantities, ratios, weights, percentages, and/or similar features and data and the like, for example, represent approximate values and can vary with the possible embodiments described and those not necessarily described but encompassed by the methodology disclosed. Unless defined otherwise, all technical and scientific terms used herein have the same meaning as commonly understood to one of ordinary skill in the art to which the invention belongs. Further, references to "a", "an", and "the" concerning any particular item, component, material, or product include plural references and are defined as at least one and could be more than one, unless the context clearly dictates otherwise. The terminology employed is for the purpose of describing particular embodiments and is not intended to be limiting in any way.

While specific embodiments have been described in detail, those with ordinary skill in the art will appreciate that various modifications and alternatives to those details could be developed in light of the overall teachings of the disclosure. Accordingly, the particular arrangements disclosed are meant to be illustrative only and not limiting as to the scope of the invention, which is to be given the full breadth of the appended claims or embodiments and any and all equivalents thereof.

REFERENCES

1. Zhao, W.; Li, S.; Yao, H.; Zhang, S.; Zhang, Y.; Yang, B.; Hou, J., Molecular Optimization Enables over 13% Efficiency in Organic Solar Cells. *J. Am. Chem. Soc.* 2017, 139, 7148-7151.
2. Gong, X.; Tong, M.; Xia, Y.; Cai, W.; Moon, J. S.; Cao, Y.; Yu, G.; Shieh, C.-L.; Nilsson, B.; Heeger, A. J., High-Detectivity Polymer Photodetectors with Spectral Response from 300 nm to 1450 nm. *Science* 2009, 325, 1665.
3. Tsutsui, Y.; Schweicher, G.; Chattopadhyay, B.; Sakurai, T.; Arlin, J.-B.; Ruzid, C.; Aliev, A.; Ciesielski, A.; Colella, S.; Kennedy, A. R.; Lemaur, V.; Olivier, Y.; Hadji, R.; Sanguinet, L.; Castet, F.; Osella, S.; Dudenko, D.; Beljonne, D.; Cornil, J.; Samori, P.; Seki, S.; Geerts, Y. H., Unraveling Unprecedented Charge Carrier Mobility through Structure Property Relationship of Four Isomers of Didodecyl[1]benzothieno[3,2-b][1]benzothiophene. *Adv. Mater.* 2016, 28, 7106-7114.
4. Tseng, H.-R.; Phan, H.; Luo, C.; Wang, M.; Perez, L. A.; Patel, S. N.; Ying, L.; Kramer, E. J.; Nguyen, T.-Q.; Bazan, G. C.; Heeger, A. J., High-Mobility Field-Effect Transistors Fabricated with Macroscopic Aligned Semiconducting Polymers. *Adv. Mater.* 2014, 26, 2993-2998.
5. McQuade, D. T.; Pullen, A. E.; Swager, T. M., Conjugated Polymer-Based Chemical Sensors. *Chem. Rev.* 2000, 100, 2537-2574.
6. Irimia-Vladu, M., "Green" electronics: biodegradable and biocompatible materials and devices for sustainable future. *Chem. Soc. Rev.* 2014, 43, 588-610.
7. Lin, P.; Yan, F., Organic Thin-Film Transistors for Chemical and Biological Sensing. *Adv. Mater.* 2012, 24, 34-51.
8. Elkington, D.; Cooling, N.; Belcher, W.; Dastoor, P. C.; Zhou, X., Organic Thin-Film Transistor (OTFT)-Based Sensors. *Electronics* 2014, 3, 234-254.
9. Mulla, M. Y.; Tuccori, E.; Magliulo, M.; Lattanzi, G.; Palazzo, G.; Persaud, K.; Torsi, L., Capacitance-modulated transistor detects odorant binding protein chiral interactions. *Nat. Commun.* 2015, 6, 6010.
10. Palazzo, G.; De Tullio, D.; Magliulo, M.; Mallardi, A.; Intranuovo, F.; Mulla, M. Y.; Favia, P.; Vikholm-Lundin, I.; Torsi, L., Detection Beyond Debye's Length with an Electrolyte-Gated Organic Field-Effect Transistor. *Adv. Mater.* 2015, 27, 911-916.
11. Torsi, L.; Magliulo, M.; Manoli, K.; Palazzo, G., Organic field-effect transistor sensors: a tutorial review. *Chem. Soc. Rev.* 2013, 42, 8612-8628.
12. Chang, J. S.; Facchetti, A. F.; Reuss, R., A Circuits and Systems Perspective of Organic/Printed Electronics: Review, Challenges, and Contemporary and Emerging Design Approaches. *IEEE Journal on Emerging and Selected Topics in Circuits and Systems* 2017, 7, 7-26.
13. Jiang, H.; Taranekar, P.; Reynolds, J. R.; Schanze, K. S., Conjugated Polyelectrolytes: Synthesis, Photophysics, and Applications. *Angew. Chem. Int. Ed.* 2009, 48, 4300-4316.
14. Thomas, S. W.; Joly, G. D.; Swager, T. M., Chemical Sensors Based on Amplifying Fluorescent Conjugated Polymers. *Chem. Rev.* 2007, 107, 1339-1386.
15. Williams, A. K.; Tropp, J.; Crater, E. R.; Eedugurala, N.; Azoulay, J. D., Thiol-Ene Click Post-Polymerization Modification of a Fluorescent Conjugated Polymer for Parts-per-Billion Pyrophosphate Detection in Seawater. *ACS Appl. Polym. Mater.* 2019, 1, 309-314.
16. Chen, L.; McBranch, D. W.; Wang, H.-L.; Helgeson, R.; Wudl, F.; Whitten, D. G., Highly Sensitive Biological and Chemical Sensors based on Reversible Fluorescence Quenching in a Conjugated Polymer. *Proc. Natl. Acad. Sci. U.S.A.* 1999, 96, 12287-12292.
17. de Silva, A. P.; Gunaratne, H. Q. N.; Gunnlaugsson, T.; Huxley, A. J. M.; McCoy, C. P.; Rademacher, J. T.; Rice, T. E., Signaling Recognition Events with Fluorescent Sensors and Switches. *Chem. Rev.* 1997, 97, 1515-1566.
18. Freudenberg, J.; Hinkel, F.; Jänsch, D.; Bunz, U. H. F., Chemical Tongues and Noses Based upon Conjugated Polymers. *Top. Curr. Chem.* 2017, 375, 67.
19. Chen, S.; Yu, Y.-L.; Wang, J.-H., Inner Filter Effect-Based Fluorescent Sensing Systems: A Review. *Anal. Chim. Acta* 2018, 999, 13-26.
20. Tanwar, A. S.; Patidar, S.; Ahirwar, S.; Dehingia, S.; Iyer, P. K., "Receptor free" inner filter effect based universal sensors for nitroexplosive picric acid using two polyfluorene derivatives in the solution and solid states. *Analyst* 2019, 144, 669-676.
21. Tanwar, A. S.; Adil, L. R.; Afroz, M. A.; Iyer, P. K., Inner Filter Effect and Resonance Energy Transfer Based Attogram Level Detection of Nitroexplosive Picric Acid Using Dual Emitting Cationic Conjugated Polyfluorene. *ACS Sens.* 2018, 3 (8), 1451-1461.
22. Tanwar, A. S.; Hussain, S.; Malik, A. H.; Afroz, M. A.; Iyer, P. K., Inner Filter Effect Based Selective Detection of Nitroexplosive-Picric Acid in Aqueous Solution and Solid Support Using Conjugated Polymer. *ACS Sens.* 2016, 1, 1070-1077.
23. Wu, M.; Sun, L.; Miao, K.; Wu, Y.; Fan, L.-J., Detection of Sudan Dyes Based on Inner-Filter Effect with Reusable Conjugated Polymer Fibrous Membranes. *ACS Appl. Mater. Interfaces* 2018, 10, 8287-8295.
24. Tropp, J.; Ihde, M. H.; Crater, E. R.; Bell, N. C.; Bhatta, R.; Johnson, I. C.; Bonizzoni, M.; Azoulay, J. D., A Sensor Array for the Nanomolar Detection of Azo Dyes in Water. *ACS Sens.* 2020, 5, 1541-1547.

What is claimed is:

1. A method of utilizing at least one n-conjugated polymer (CP) for the detection of one or more analytes through the inner filter effect, the method comprising:
   mixing the at least one n-conjugated polymer with an analyte in a solution;
   applying electromagnetic radiation to the solution, wherein the radiation or fluorescence of the n-conjugated polymer is altered or attenuated by the analyte;
   measuring the attenuated radiation or fluorescence from the polymer to obtain fluorescence data;
   processing and analyzing by at least one algorithm the attenuated radiation or fluorescence data to detect the presence and/or the type of the analyte; and
   wherein the method excludes immobilizing and incorporating the conjugated polymer in a solid state material for detection of the analyte,
   wherein the n-conjugated polymer has the following structure wherein a 9H-fluorene group is bonded to an unsaturated linker:

wherein n is 5 to 10,000 and the 9H-fluorene group is bonded to the unsaturated linker in a reaction including:

2. The method of claim 1, wherein the n-conjugated polymer varies in size or molecular weight with at least one other utilized n-conjugated polymer.

3. The method of claim 1, wherein single or multiple analytes are discriminated utilizing at least one multivariate pattern recognition algorithm.

4. The method of claim 3, wherein the measured attenuated radiation or fluorescence from the polymer is processed and/or analyzed by an algorithm that comprises at least one machine learning algorithm and wherein the algorithm is processed by a microprocessor-based device.

5. The method of claim 3, wherein the discrimination of multiple analytes is visualized by an algorithm that comprises at least one machine learning algorithm.

6. The method of claim 1, wherein the solution is static.

7. The method of claim 1, wherein the solution is dynamic and flows.

8. A method of utilizing at least one n-conjugated polymer (CP) for the detection of one or more analytes through the inner filter effect, the method comprising:
  placing the at least one n-conjugated polymer in a first solution and placing an analyte in a second solution, wherein the polymer does not mix with or touch the analyte and wherein the first solution is static and the second solution is dynamic, or vice versa, or, alternatively, both solutions are static or both solutions are dynamic;
  applying electromagnetic radiation to both of the first and second solutions, whereby the radiation or fluorescence of the n-conjugated polymer is altered or attenuated by the analyte;
  measuring the attenuated radiation or fluorescence from the polymer to obtain fluorescence data; and
  processing and analyzing by at least one algorithm the attenuated radiation or fluorescence data to detect the presence and/or the type of the analyte; and
  wherein the method excludes immobilizing and incorporating the conjugated polymer in a solid state material for detection of the analyte.

9. The method of claim 8, wherein the first solution consists of or is made of a different solvent than the second solution.

10. The method of claim 8, wherein the n-conjugated polymer has the formula:

where Ar is an arene or (hetero)arene; R is selected from the group consisting of: variable length, linear or branched, aliphatic ethylene glycol chains or halogen-containing or heteroatom-containing chains of length n, where n is an integer value, unsubstituted hydrocarbyl, substituted hydrocarbyl, unsubstituted aryl, substituted aryl, unsubstituted heteroaryl, substituted heteroaryl, unsubstituted hydrocarbylene, hydrocarbyl, and substituted hydrocarbylene, hydrocarbyl, $R^2F$, $R^2Cl$, $R^2Br$, $R^2I$, $R^2CN$, $—R^2$, $—R^2OH$, $—R^2OR^3$, $—R^2COOH$, $—R^2COOR^3$, $—R^2NH_2$, $—R^2NHR^3$, $R^2NR^3R^4$, $—R^2SO_3^-$, $—R^2NH_3^+$, or $—R^2COO^-$, and other charged functionalities, where $R^2$, $R^3$, and $R^4$ are independently selected from a hydrocarbyl group or an ethylene glycol-based group; R can be any functional group; and n is an integer between about 10 and about 1000.

11. The method of claim 8, wherein the copolymer has the formula:

where Ar and $Ar_2$ are arenes or (hetero)arenes and where Ar and $Ar_2$ are different in identity; R is selected from the group consisting of: variable length, linear or branched, aliphatic ethylene glycol chains or halogen-containing or heteroatom-containing chains of length n, where n is an integer value, unsubstituted hydrocarbyl, substituted hydrocarbyl, unsubstituted aryl, substituted aryl, unsubstituted heteroaryl, substituted heteroaryl, unsubstituted hydrocarbylene, hydrocarbyl, and substituted hydrocarbylene, hydrocarbyl, $R^2F$, $R^2Cl$, $R^2Br$, $R^2I$, $R^2CN$, $—R^2$, $—R^2OH$, $—R^2OR^3$, $—R^2COOH$, $—R^2COOR^3$, $—R^2NH_2$, $—R^2NHR^3$, $R^2NR^3R^4$, $—R^2SO_3^-$, $—R^2NH_3^+$, or $—R^2COO^-$, and other charged functionalities, where $R^2$, $R^3$, and $R^4$ are independently selected from a hydrocarbyl group or an ethylene glycol-based group; R can be any functional group; and n is an integer between about 10 and about 1000.

12. The method of claim 8, wherein the conjugated polymer has the formula:

where UL is an unsaturated linker such as an alkyne or optionally substituted alkene unit that connects substituted arenes, substituted heteroarenes, unsubstituted arenes, unsubstituted heteroarenes, or a combination thereof; R is selected from the group consisting of: variable length, linear or branched, aliphatic ethylene glycol chains or halogen-containing or heteroatom-containing chains of length n, where n is an integer value, unsubstituted hydrocarbyl, substituted hydrocarbyl, unsubstituted aryl, substituted aryl, unsubstituted heteroaryl, substituted heteroaryl, unsubstituted hydrocarbylene, hydrocarbyl, and substituted hydrocarbylene, hydrocarbyl, $R^2F$, $R^2Cl$, $R^2Br$, $R^2I$, $R^2CN$, $-R^2$, $-R^2OH$, $-R^2OR^3$, $-R^2COOH$, $-R^2COOR^3$, $-R^2NH_2$, $-R^2NHR^3$, $R^2NR^3R^4$, $-R^2SO_3^-$, $-R^2NH_3^+$, or $-R^2COO^-$, and other charged functionalities, where $R^2$, $R^3$, and $R^4$ are independently selected from a hydrocarbyl group or an ethylene glycol-based group; R can be any functional group; and n is an integer between about 10 and about 1000.

13. The method of claim 8, wherein the first solution and the second solution consist of or are made of the same solvent.

14. The method of claim 8, wherein the n-conjugated polymer has the following structure wherein a 9H-fluorene group is bonded to an unsaturated linker:

wherein n is 5 to 10,000 and the 9H-fluorene group is bonded to the unsaturated linker in a reaction including:

P1

P2

P3

* * * * *

UNITED STATES PATENT AND TRADEMARK OFFICE
CERTIFICATE OF CORRECTION

PATENT NO. : 11,781,986 B2
APPLICATION NO. : 17/139707
DATED : October 10, 2023
INVENTOR(S) : Tropp et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 97 days.

Signed and Sealed this
Twelfth Day of November, 2024

*Katherine Kelly Vidal*

Katherine Kelly Vidal
*Director of the United States Patent and Trademark Office*